United States Patent
Matsumoto et al.

(10) Patent No.: US 12,383,239 B2
(45) Date of Patent: Aug. 12, 2025

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventors: Tsuyoshi Matsumoto, Tokyo (JP); Tomoki Inoue, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/419,525

(22) Filed: Jan. 22, 2024

(65) Prior Publication Data

US 2024/0188936 A1 Jun. 13, 2024

Related U.S. Application Data

(63) Continuation of application No. PCT/JP2022/028735, filed on Jul. 26, 2022.

(30) Foreign Application Priority Data

Aug. 17, 2021 (JP) ................. 2021-132614

(51) Int. Cl.
*A61B 8/00* (2006.01)
*A61B 8/08* (2006.01)

(52) U.S. Cl.
CPC ............ *A61B 8/5253* (2013.01); *A61B 8/085* (2013.01); *A61B 8/462* (2013.01); *A61B 8/463* (2013.01); *A61B 8/54* (2013.01); *A61B 8/4488* (2013.01)

(58) Field of Classification Search
CPC ....... A61B 8/5253; A61B 8/085; A61B 8/462; A61B 8/463; A61B 8/54; A61B 8/4488;
(Continued)

(56) References Cited

U.S. PATENT DOCUMENTS

| | | | |
|---|---|---|---|
| 2006/0241435 A1* | 10/2006 | Koga | A61B 8/462 600/437 |
| 2016/0350503 A1* | 12/2016 | Jun | A61B 8/465 |
| 2016/0367221 A1 | 12/2016 | Igarashi et al. | |

FOREIGN PATENT DOCUMENTS

| | | |
|---|---|---|
| JP | 2005-323925 A | 11/2005 |
| JP | 2010-057562 A | 3/2010 |

(Continued)

OTHER PUBLICATIONS

International Search Report issued in PCT/JP2022/028735; mailed Sep. 27, 2022.
(Continued)

*Primary Examiner* — Bo Joseph Peng
(74) *Attorney, Agent, or Firm* — Studebaker Brackett PLLC

(57) ABSTRACT

In an ultrasound diagnostic apparatus and a control method of the ultrasound diagnostic apparatus of the present invention, a panoramic image generation unit generates a panoramic image from ultrasound image data or ultrasound images of a plurality of frames included in the same tomographic plane formed by moving an ultrasound probe. A hidden region detection unit detects whether or not a hidden region that is not displayed on a display screen is present in the panoramic image, a blood vessel detection unit detects a blood vessel in the panoramic image, and a notification unit notifies of a message in a case where it is detected that the hidden region is present and it is detected that the blood vessel is present in the hidden region. Accordingly, the user can easily understand a state of the blood vessel in the hidden region of the panoramic image in a case of performing the blood vessel puncture while observing the panoramic image.

20 Claims, 7 Drawing Sheets

(58) Field of Classification Search
CPC ..... A61B 8/429; A61B 8/5223; A61B 8/5246; A61B 8/0891; A61B 8/14; A61B 8/4254
See application file for complete search history.

(56) References Cited

FOREIGN PATENT DOCUMENTS

| | | |
|---|---|---|
| JP | 2013-165923 A | 8/2013 |
| JP | 2017-006655 A | 1/2017 |
| JP | 2018-051346 A | 4/2018 |

OTHER PUBLICATIONS

International Preliminary Report On Patentability (Chapter I) and Written Opinion of the International Searching Authority issued in PCT/JP2022/028735; issued Feb. 13, 2024.

* cited by examiner

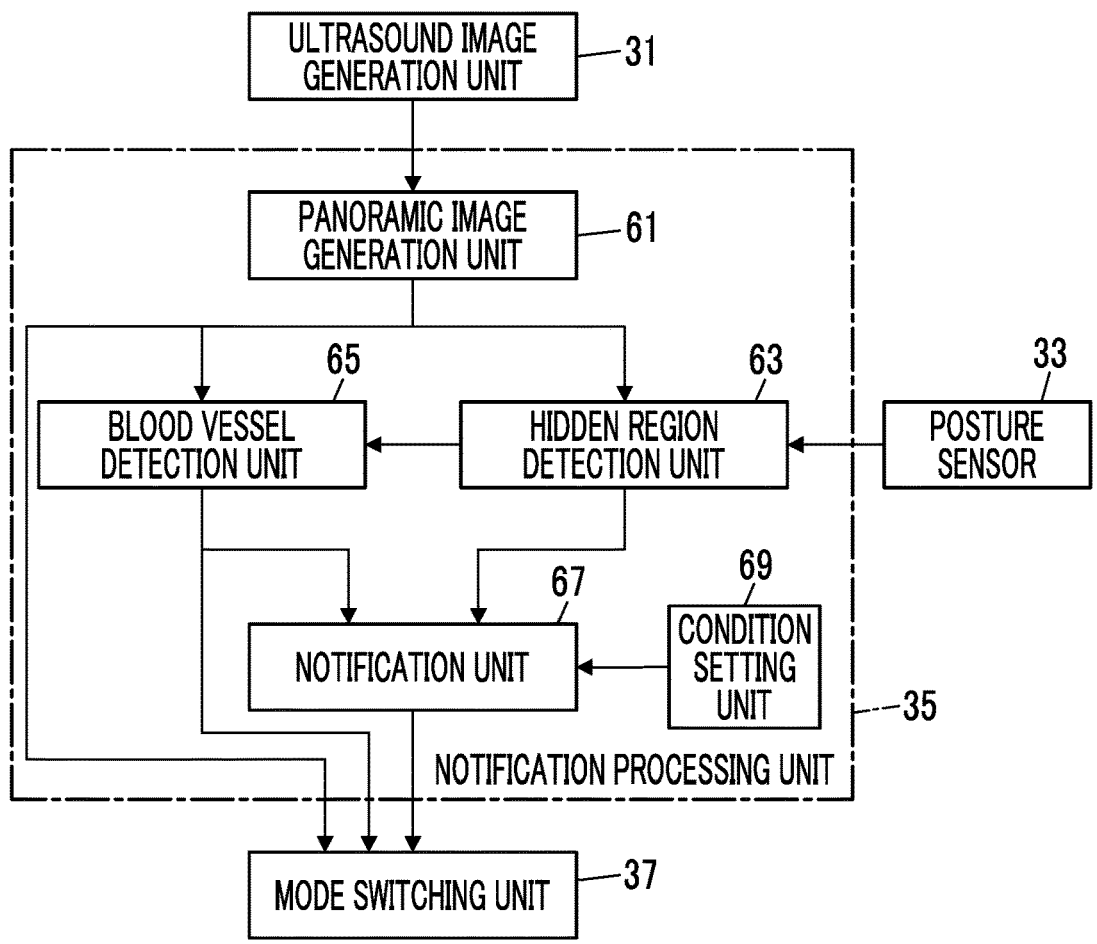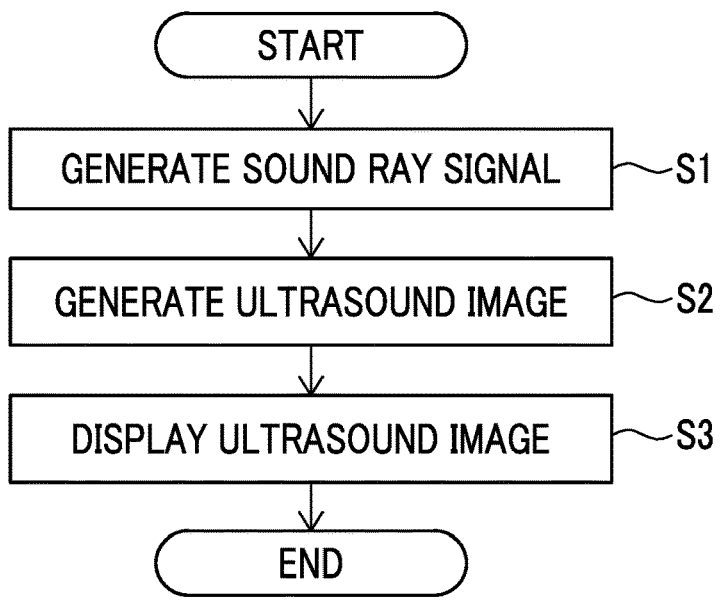

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of PCT International Application No. PCT/JP2022/028735 filed on Jul. 26, 2022, which claims priority under 35 U.S.C. § 119(a) to Japanese Patent Application No. 2021-132614 filed on Aug. 17, 2021. The above applications are hereby expressly incorporated by reference, in their entirety, into the present application.

BACKGROUND OF THE INVENTION

1. Field of the Invention

The present invention relates to an ultrasound diagnostic apparatus and a control method of the ultrasound diagnostic apparatus which have a function of generating and displaying a panoramic image from ultrasound images of a plurality of frames.

2. Description of the Related Art

In a case where blood vessel puncture is performed using an ultrasound diagnostic apparatus, a technique is performed which searches an ultrasound image displayed on a monitor for a blood vessel with appropriate size and depth for puncture and placement of a catheter, carefully observes and analyzes whether or not the blood vessel can be safely punctured with a puncture needle, for example, whether or not there is a peripheral tissue such as a nerve, an artery, and an organ around the blood vessel, and whether or not there is a lesion, a blood clot, or the like, and actually performs the puncture with the puncture needle in a case where it is determined that the blood vessel can be safely punctured with the puncture needle.

In a case of searching for the blood vessel with the appropriate size and depth for the puncture and placement of the catheter, a user (examiner) of the ultrasound diagnostic apparatus needs to select one blood vessel from among many blood vessels present in the ultrasound image. However, since display screens of many monitors are rectangular, and a length in an up and down direction (vertical direction) differs from a length in a left and right direction (lateral direction), the ultrasound images are displayed to fit within the display screen in the ultrasound diagnostic apparatus in the related art.

For example, in a case where a monitor 41 is changed from a state where a laterally long ultrasound image 74 is displayed in an enlarged manner to fit within a display screen 72 of the monitor 41 in a laterally long posture as illustrated in FIG. 12A, to a vertically long posture by the user, it is common practice to reduce and display the ultrasound image 74 such that the laterally long ultrasound image 74 fits within the display screen 72 of the monitor 41 in the vertically long posture without changing an aspect ratio of the ultrasound image 74, as illustrated in FIG. 12B.

Here, as prior art documents used as references of the present invention, there are ultrasound imaging devices that perform various kinds of processing according to the orientation of the monitor as in JP2005-323925A, JP2010-057562A, and JP2013-165923A.

JP2005-323925A discloses an ultrasound imaging device that detects the rotation of a display unit in the display screen from positional information of a flat panel type display unit measured by a position sensor, and optimizes image information to be displayed on the display screen of the display unit according to the rotation.

JP2010-057562A discloses an ultrasound diagnostic apparatus that detects a posture change of a housing, and controls generation of an ultrasound image according to the posture change of the housing.

JP2013-165923A discloses an ultrasound diagnostic apparatus that detects a posture or a posture change of an apparatus main body, and changes contents of an image to be displayed on a display surface of a portable apparatus main body on the basis of the posture or the posture change of the apparatus main body.

SUMMARY OF THE INVENTION

For example, in a case where it is desired to observe an ultrasound image over a wider range than one frame of an ultrasound image in a width direction, it is necessary to sequentially generate ultrasound images while moving an ultrasound probe in the width direction, and to generate a panoramic image from the ultrasound images of the plurality of frames.

However, in order for the user to check blood vessels in a case of performing blood vessel puncture, in a case where the panoramic image is enlarged and displayed, only a partial region of the panoramic image that is enlarged and displayed can be displayed in real time. Therefore, there is a problem in that, in the panoramic image, the user can easily check the blood vessel in the display region that is displayed on the display screen, but cannot understand a state of the blood vessel in the hidden region that is not displayed on the display screen.

Therefore, an object of the present invention is to provide an ultrasound diagnostic apparatus and a control method of the ultrasound diagnostic apparatus which allows the user to easily understand a state of the blood vessel in the hidden region of the panoramic image in a case of performing the blood vessel puncture while observing the panoramic image.

In order to achieve the object, an aspect of the present invention provides an ultrasound diagnostic apparatus including an ultrasound probe; an ultrasound image generation unit that generates an ultrasound image from ultrasound image data obtained by performing transmission and reception of an ultrasound beam with respect to an examination location of a subject using the ultrasound probe; a panoramic image generation unit that generates a panoramic image from the ultrasound image data or ultrasound images of a plurality of frames included in the same tomographic plane formed by moving the ultrasound probe; a monitor that has a display screen; a display control unit that displays the panoramic image on the display screen; a hidden region detection unit that detects whether or not a hidden region that is not displayed on the display screen is present in the panoramic image; a blood vessel detection unit that detects a blood vessel in the panoramic image; and a notification unit that notifies of a message in a case where it is detected that the hidden region is present and it is detected that the blood vessel is present in the hidden region.

Here, it is preferable that the panoramic image generation unit generates the panoramic image from the ultrasound image data or ultrasound images of the plurality of frames generated by moving the ultrasound probe in a width direction of a transducer array of the ultrasound probe along a body surface of the examination location in a state where the ultrasound probe is in contact with the body surface.

In addition, it is preferable that the panoramic image generation unit generates the panoramic image from the ultrasound image data or ultrasound images of the plurality of frames generated by moving the ultrasound probe in a direction from a body surface toward an inside of a body of the examination location or in a direction from the inside of the body toward the body surface in a state where the ultrasound probe is in contact with the body surface of the examination location.

In addition, it is preferable that the panoramic image generation unit performs image analysis on the ultrasound image data or ultrasound images of the plurality of frames, and generates the panoramic image from the ultrasound image data or ultrasound images of the plurality of frames on the basis of a result of the image analysis, and the hidden region detection unit detects whether or not the hidden region is present by aligning the panoramic image and the ultrasound image of a current frame on the basis of the result of the image analysis.

In addition, it is preferable that the ultrasound probe includes a motion sensor that detects a motion of the ultrasound probe, the panoramic image generation unit performs image analysis on the ultrasound image data or ultrasound images of the plurality of frames, and generates the panoramic image from the ultrasound image data or ultrasound images of the plurality of frames on the basis of a result of the image analysis and the motion of the ultrasound probe, and the hidden region detection unit detects whether or not the hidden region is present by aligning the panoramic image and the ultrasound image of a current frame on the basis of the result of the image analysis and the motion of the ultrasound probe.

In addition, it is preferable that the panoramic image generation unit generates the panoramic image from the ultrasound image data or ultrasound images of the plurality of frames generated within a certain period from the present to the past.

In addition, it is preferable that the panoramic image generation unit generates the panoramic image from the ultrasound image data or ultrasound images of the plurality of frames generated within one examination period for performing an examination on the examination location.

In addition, it is preferable that the panoramic image generation unit generates the panoramic image from the ultrasound image data or ultrasound images of the plurality of frames generated within one contact period in which the ultrasound probe is in contact with a body surface of the examination location.

In addition, it is preferable that, in a case where the ultrasound image data or ultrasound image of a current frame is ultrasound image data or an ultrasound image of the same tomographic plane as the panoramic image, the panoramic image generation unit updates the panoramic image using the ultrasound image data or ultrasound image of the current frame.

In addition, it is preferable that, in a case where it is detected that the blood vessel is present in the hidden region, the notification unit notifies of a message indicating a direction of the blood vessel in the hidden region.

In addition, it is preferable that, in a case where it is detected that the blood vessel is present in the hidden region, the notification unit notifies of a message for an instruction of displaying the panoramic image in a reduced manner.

In addition, it is preferable that, in a case where it is detected that the hidden region is present in a part on a lower side of the panoramic image in a depth direction, the notification unit notifies of a message for an instruction of changing depth setting of the ultrasound image.

In addition, it is preferable that an orientation of the monitor is changeable to a vertically long posture or a laterally long posture, the ultrasound diagnostic apparatus further includes a posture sensor that detects whether the orientation of the monitor is the vertically long posture or the laterally long posture, and in a case where it is detected that the monitor is in the vertically long posture and it is detected that the hidden region is present in a part of the panoramic image in a width direction, or in a case where it is detected that the monitor is in the laterally long posture and it is detected that the hidden region is present in a part of the panoramic image in a depth direction, the notification unit notifies of a message for an instruction of changing the orientation of the monitor between the vertically long posture and the laterally long posture.

In addition, it is preferable that the notification unit notifies of a message for an instruction of moving the ultrasound probe in a direction of the blood vessel in the hidden region.

In addition, it is preferable that, in a case where it is detected that the blood vessel is present in a display region and it is not detected that a blood vessel is present in the hidden region, the notification unit does not notify of the message.

In addition, it is preferable that the ultrasound diagnostic apparatus further includes a condition setting unit that sets a condition for a blood vessel as a puncture target, in which, in a case where it is detected that the blood vessel is present in a display region and the hidden region, the notification unit notifies of the message on the basis of a comparison result between the blood vessel in the display region and the hidden region and the condition.

In addition, it is preferable that, in a case where it is not detected that a blood vessel is present in a display region and it is detected that the blood vessel is present in the hidden region, the notification unit notifies of the message.

In addition, it is preferable that, in a case where it is not detected that a blood vessel is present in a display region and the hidden region, the notification unit notifies of a message indicating that no blood vessel is detected.

Further, another aspect of the present invention provides a control method of an ultrasound diagnostic apparatus, the control method including a step of generating an ultrasound image from ultrasound image data obtained by performing transmission and reception of an ultrasound beam with respect to an examination location of a subject using an ultrasound probe, via an ultrasound image generation unit; a step of generating a panoramic image from the ultrasound image data or ultrasound images of a plurality of frames included in the same tomographic plane formed by moving the ultrasound probe, via a panoramic image generation unit; a step of displaying the panoramic image on the display screen of a monitor, via a display control unit; a step of detecting whether or not a hidden region that is not displayed on the display screen is present in the panoramic image, via a hidden region detection unit; a step of detecting a blood vessel in the panoramic image, via a blood vessel detection unit; and a step of notifying of a message, via a notification unit, in a case where it is detected that the hidden region is present and it is detected that the blood vessel is present in the hidden region.

In the present invention, in a case where it is detected that a hidden region that is not displayed on the display screen is present in the panoramic image and it is detected that a blood vessel is present in the hidden region, a message is notified.

Accordingly, according to the present invention, since the user can easily understand the state of the blood vessel in the hidden region by displaying the blood vessel in the hidden region according to the content of the message, it is possible to safely and reliably perform the blood vessel puncture.

BRIEF DESCRIPTION OF THE DRAWINGS

FIG. 4 is a block diagram of an embodiment illustrating a configuration of a notification processing unit.

FIG. 5 is a flowchart of an embodiment illustrating an operation of an ultrasound diagnostic apparatus in a case of generating an ultrasound image.

DESCRIPTION OF THE PREFERRED EMBODIMENTS

Hereinafter, an ultrasound diagnostic apparatus and a control method of the ultrasound diagnostic apparatus according to an embodiment of the present invention will be described in detail on the basis of preferred embodiments illustrated in the accompanying drawings.

Figure 1:
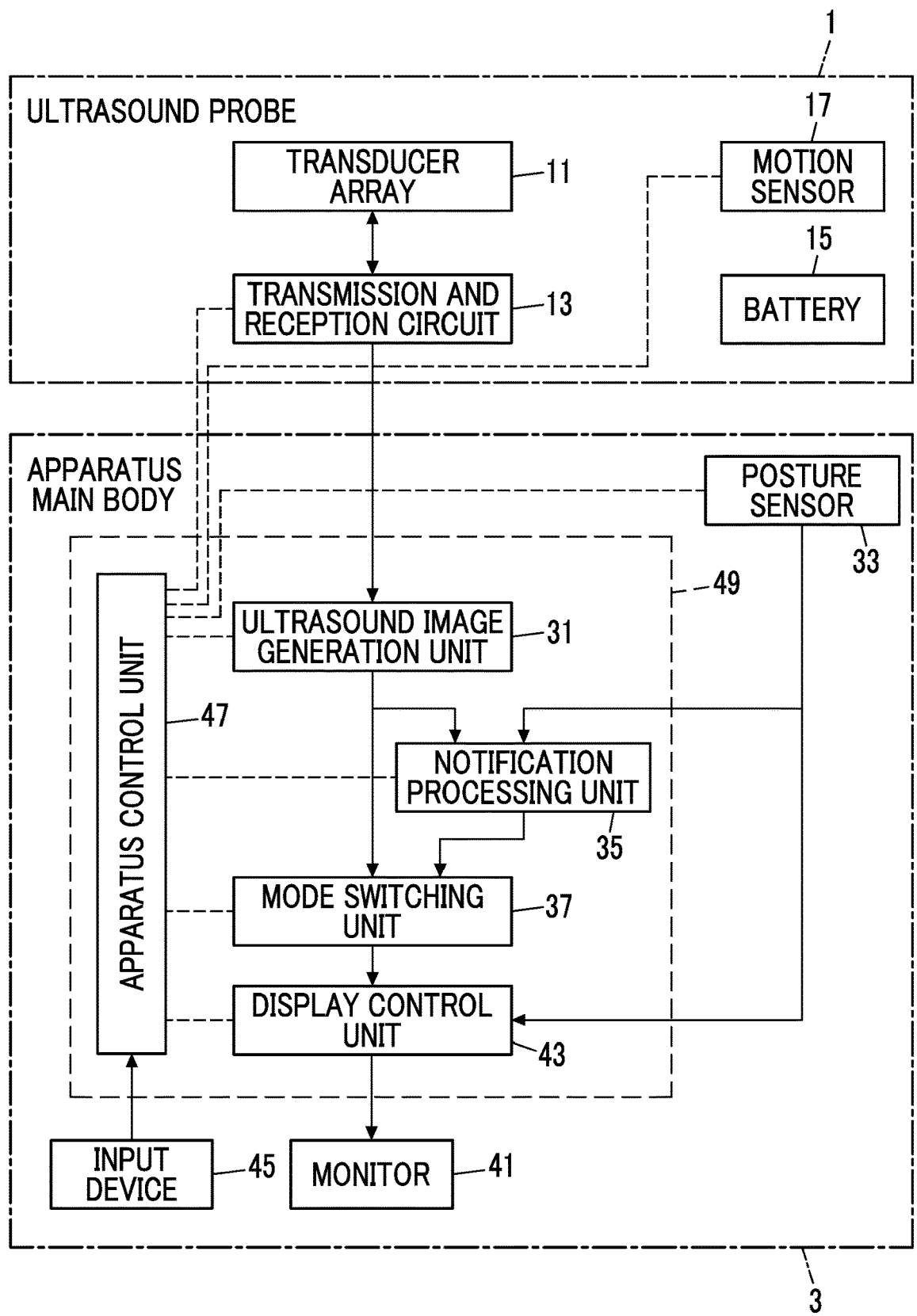
FIG. 1 is a block diagram of an embodiment illustrating a configuration of an ultrasound diagnostic apparatus of the present invention.

FIG. 1 is a block diagram of an embodiment illustrating a configuration of an ultrasound diagnostic apparatus of the present invention. The ultrasound diagnostic apparatus illustrated in FIG. 1 is a handheld ultrasound diagnostic apparatus, and includes an ultrasound probe 1, and an apparatus main body 3 connected to the ultrasound probe 1. The ultrasound diagnostic apparatus of the present embodiment is realized by the ultrasound probe 1, the handheld apparatus main body 3, and an ultrasound diagnosis application program running on the apparatus main body 3.

The ultrasound probe 1 scans an examination location of a subject using an ultrasound beam, and outputs a sound ray signal corresponding to an ultrasound image of the examination location. As illustrated in FIG. 1, the ultrasound probe 1 includes a transducer array 11, a transmission and reception circuit 13, a motion sensor 17, and a battery 15. The transducer array 11 and the transmission and reception circuit 13 are bidirectionally connected to each other, and an apparatus control unit 47 of the apparatus main body 3, which will be described later, is connected to the transmission and reception circuit 13 and the motion sensor 17.

The transducer array 11 has a plurality of ultrasonic transducers arranged in a one-dimensional or two-dimensional manner. According to a drive signal supplied from the transmission and reception circuit 13, each of the transducers transmits an ultrasonic wave and receives a reflected wave from the subject to output an analog reception signal.

For example, each transducer is formed by using an element in which electrodes are formed at both ends of a piezoelectric body consisting of piezoelectric ceramic typified by lead zirconate titanate (PZT), a polymer piezoelectric element typified by poly vinylidene di fluoride (PVDF), piezoelectric single crystal typified by lead magnesium niobate-lead titanate (PMN-PT), or the like.

Figure 2:
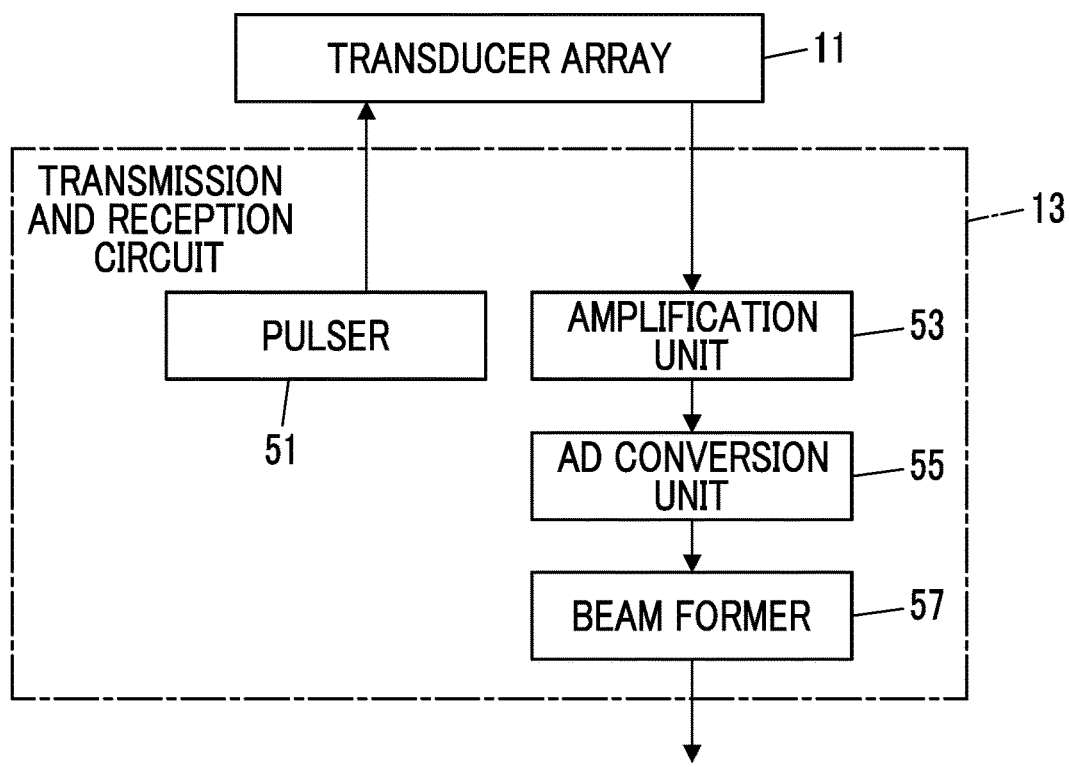
FIG. 2 is a block diagram of an embodiment illustrating a configuration of a transmission and reception circuit.

The transmission and reception circuit 13 causes the transducer array 11 to transmit the ultrasound beam, and performs reception focusing processing on the reception signal output from the transducer array 11 that has received the ultrasound echo to generate a sound ray signal, under the control of the apparatus control unit 47. As illustrated in FIG. 2, the transmission and reception circuit 13 has a pulser 51 connected to the transducer array 11, and an amplification unit 53, an analog digital (AD) conversion unit 55, and a beam former 57 that are sequentially connected in series from the transducer array 11.

The pulser 51 includes, for example, a plurality of pulse generators, and the pulser 51 performs transmission focusing processing of adjusting the amount of delay of each drive signal so that ultrasonic waves transmitted from the plurality of transducers of the transducer array 11 form an ultrasound beam on the basis of a transmission delay pattern selected by the apparatus control unit 47, and supplying the obtained signals to the plurality of transducers. By this transmission focusing processing, in a case where a pulsed or continuous-wave voltage is applied to the electrodes of the transducers of the transducer array 11, the piezoelectric body expands and contracts to generate pulsed or continuous-wave ultrasonic waves from each transducer. From the combined wave of these ultrasonic waves, an ultrasound beam is formed.

The transmitted ultrasound beam is reflected by a target, for example, a site of the subject, and propagates toward the transducer array 11 of the ultrasound probe 1. Each transducer constituting the transducer array 11 expands and contracts by receiving the ultrasound echo propagating toward the transducer array 11 in this manner, to generate the reception signal that is an electric signal, and outputs the reception signal to the amplification unit 53.

The amplification unit 53 amplifies the signals input from each transducer constituting the transducer array 11, and transmits the amplified signals to the AD conversion unit 55. The AD conversion unit 55 converts the analog signal transmitted from the amplification unit 53 into digital reception data, and outputs the reception data to the beam former 57.

The beam former 57 performs reception focusing processing in which addition is performed by giving delays to respective pieces of the reception data converted by the AD conversion unit 55 according to a sound speed distribution or a sound speed set on the basis of a reception delay pattern selected by the apparatus control unit 47. Through the reception focusing processing, a sound ray signal in which each piece of the reception data converted by the AD conversion unit 55 is phased and added and the focus of the ultrasound echo is narrowed is generated.

The motion sensor 17 detects the motion of the ultrasound probe 1 under the control of the apparatus control unit 47.

The motion sensor 17 is not particularly limited as long as the motion or position of the ultrasound probe 1 can be detected, and examples of the motion sensor 17 include an acceleration sensor that detects the motion of the ultrasound probe 1, a gravity sensor that detects the gravity, and a gyro sensor that detects the rotation of the ultrasound probe 1.

The battery 15 is built in the ultrasound probe 1, and supplies power to each circuit of the ultrasound probe 1.

Next, the apparatus main body 3 generates and displays the ultrasound image of the examination location of the subject on the basis of the sound ray signal generated by the ultrasound probe 1. The apparatus main body 3 is, for example, a handheld terminal device such as a smartphone or a tablet personal computer (PC), and includes an ultrasound image generation unit 31, a posture sensor 33, a notification processing unit 35, a mode switching unit 37, a monitor 41, a display control unit 43, an input device 45, and the apparatus control unit 47 as illustrated in FIG. 1.

The ultrasound image generation unit 31 is connected to the transmission and reception circuit 13 of the ultrasound probe 1, and each of the notification processing unit 35 and the mode switching unit 37 is connected to the ultrasound image generation unit 31. Each of the notification processing unit 35 and the display control unit 43 is connected to the posture sensor 33. The mode switching unit 37 is connected to the notification processing unit 35, and the display control unit 43 and the monitor 41 are sequentially connected to the mode switching unit 37. The apparatus control unit 47 is connected to the ultrasound image generation unit 31, the posture sensor 33, the notification processing unit 35, the mode switching unit 37, and the display control unit 43, and the input device 45 is connected to the apparatus control unit 47.

The ultrasound probe 1 and the apparatus main body 3 are wirelessly connected by wireless communication such as Wireless Fidelity (Wi-Fi), or are connected in a wired manner by wired communication such as a Universal Serial Bus (USB) cable.

Figure 3:
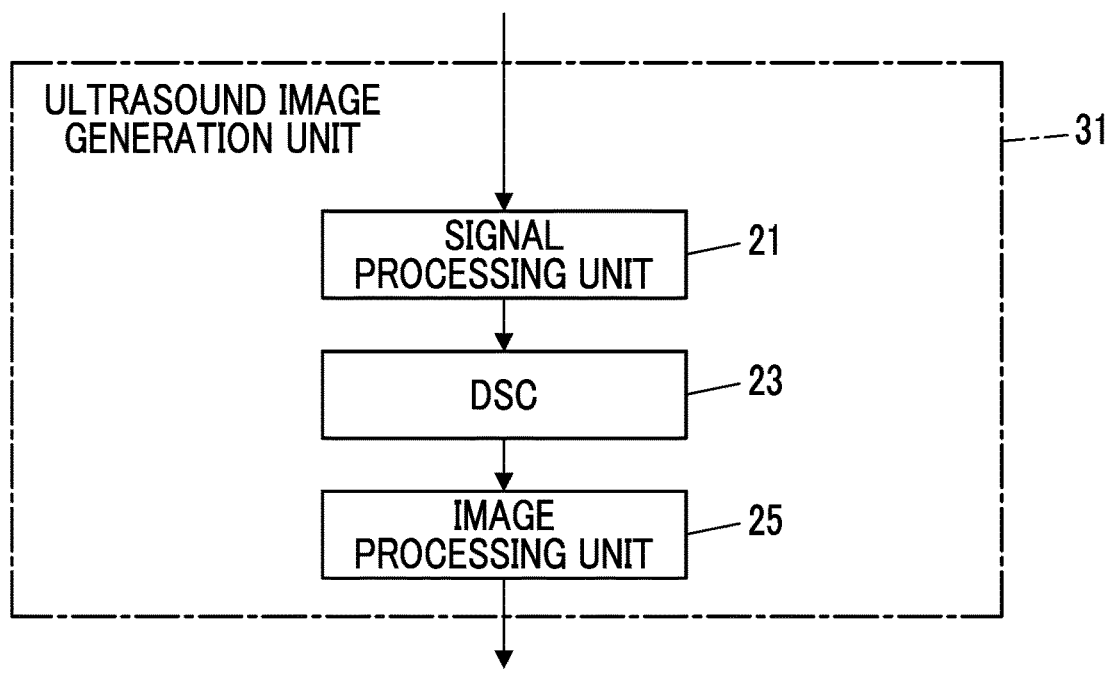
FIG. 3 is a block diagram of an embodiment illustrating a configuration of an ultrasound image generation unit.

The ultrasound image generation unit 31 generates the ultrasound image (ultrasound image signal) of the examination location of the subject, from ultrasound image data, that is, the sound ray signal in the present embodiment, obtained by performing transmission and reception of the ultrasound beams with respect to the examination location of the subject using the ultrasound probe 1 (more precisely, transducer array 11), under the control of the apparatus control unit 47. As illustrated in FIG. 3, the ultrasound image generation unit 31 has a configuration in which a signal processing unit 21, a digital scan converter (DSC) 23, and an image processing unit 25 are sequentially connected in series.

Note that the ultrasound image data may be a signal or data before the ultrasound image is generated, and the ultrasound image generation unit 31 may generate, as the ultrasound image data, the ultrasound image from the signal or the data before the ultrasound image is generated from the reception signal.

The signal processing unit 21 generates image information data corresponding to the ultrasound image on the basis of the sound ray signal generated by the transmission and reception circuit 13. More specifically, the signal processing unit 21 generates the image information data representing tomographic image information regarding tissues inside the subject, by performing envelope detection processing after signal processing, for example, correcting the attenuation of the sound ray signal generated by the beam former 57 of the transmission and reception circuit 13, which is caused by the propagation distance according to the depth of the reflection position of the ultrasonic wave.

The DSC 23 raster-converts the image information data generated by the signal processing unit 21 into an image signal according to a normal television signal scanning method.

The image processing unit 25 performs various kinds of image processing such as brightness correction, gradation correction, sharpness correction, image size correction, refresh rate correction, scanning frequency correction, and color correction according to a display format of the monitor 41, on the image signal input from the DSC 23 to generate the ultrasound image, and then outputs the ultrasound image on which the image processing has been performed, to the display control unit 43.

The monitor (display unit) 41 has a rectangular display screen, is configured such that the orientation can be changed to a vertically long posture in which the display screen is in a vertically long state or a laterally long posture in which the display screen is in a laterally long state by the user rotating the apparatus main body 3 by 90 degrees around an axis perpendicular to the display screen, and displays various kinds of information under the control of the display control unit 43.

The monitor 41 is not particularly limited, but for example, a liquid crystal display (LCD), an organic electroluminescence (EL) display, and the like can be exemplified.

The posture sensor 33 detects whether the orientation (posture) of the monitor 41, that is, the orientation (posture) of the apparatus main body 3 in the present embodiment is the vertically long posture or the laterally long posture, under the control of the apparatus control unit 47.

The posture sensor 33 is not particularly limited as long as the orientation of the monitor 41 can be detected, and examples of the posture sensor 33 include an acceleration sensor that detects the motion of the apparatus main body 3, a gravity sensor that detects the gravity, and a gyro sensor that detects the rotation of the apparatus main body 3.

The notification processing unit 35 performs various kinds of processing for performing a notification regarding the blood vessel, under the control of the apparatus control unit 47. As illustrated in FIG. 4, the notification processing unit 35 has a panoramic image generation unit 61, a hidden region detection unit 63, a blood vessel detection unit 65, a notification unit 67, and a condition setting unit 69.

The panoramic image generation unit 61 is connected to the ultrasound image generation unit 31, and each of the hidden region detection unit 63 and the blood vessel detection unit 65 is connected to the panoramic image generation unit 61. The hidden region detection unit 63 is connected to the posture sensor 33, and the blood vessel detection unit 65 is connected to the hidden region detection unit 63. The notification unit 67 is connected to each of the hidden region detection unit 63, the blood vessel detection unit 65, and the condition setting unit 69. The mode switching unit 37 is connected to each of the panoramic image generation unit 61, the blood vessel detection unit 65, and the notification unit 67.

The panoramic image generation unit 61 generates a panoramic image from the ultrasound images of the plurality of frames included in the same tomographic plane formed by moving the ultrasound probe 1.

For example, the panoramic image generation unit 61 can generate the panoramic image from the ultrasound images of the plurality of frames that are generated by moving the ultrasound probe 1 in a state where the ultrasound probe 1 is in contact with the body surface of the examination location, in the width direction of the transducer array 11 of the ultrasound probe 1 along the body surface, in other words, in the arrangement direction of the transducer array 11 of the ultrasound probe 1 corresponding to the width direction of the ultrasound image.

In addition, the panoramic image generation unit 61 can generate the panoramic image from the ultrasound images of the plurality of frames that are generated by moving the ultrasound probe 1 in a state where the ultrasound probe 1 is in contact with the body surface of the examination location, in a direction from the body surface toward the inside of the body of the examination location by pressing the body surface of the examination location of the subject, or in a direction from the inside of the body toward the body surface by relaxing the pressing on the body surface.

The same tomographic plane is one tomographic plane formed by moving the ultrasound probe 1, in other words, does not include two or more different tomographic planes formed by moving the ultrasound probe 1.

The panoramic image is generated from at least two frames of ultrasound images having different observation ranges. The observation range is a range of the examination location included in the ultrasound images generated at different positions in the same tomographic plane of the human body (examination site) by moving the ultrasound probe 1.

Note that the panoramic image generation unit 61 may generate the panoramic image from the ultrasound images of the plurality of frames as in the present embodiment, or may generate the panoramic image from the ultrasound image data of a plurality of frames before the ultrasound image is generated. In other words, the panoramic image generation unit 61 may generate the panoramic image from the ultrasound image data or ultrasound images of the plurality of frames. The same applies to the following description regarding the panoramic image generation unit 61.

The hidden region detection unit 63 detects whether or not the hidden region that is not displayed on the display screen of the monitor 41 is present in the panoramic image generated by the panoramic image generation unit 61.

The hidden region is a region of the panoramic image, which is not displayed on the display screen in a case where the panoramic image is displayed on the display screen of the monitor 41. On the other hand, a region of the panoramic image, which is displayed on the display screen, is referred to as a display region.

In a case of a panoramic blood vessel detection mode described later, the blood vessel detection unit 65 detects the blood vessel in the panoramic image by analyzing the panoramic image.

The blood vessel detection unit 65 detects short-axis views of all the blood vessels in the panoramic image, for example. The short-axis view of the blood vessel is an image of a cross section obtained by slicing the blood vessel in a cross-sectional direction perpendicular to a running direction of the blood vessel. Therefore, the short-axis view of the blood vessel represents a region (blood vessel region) of the cross section of the blood vessel in the cross-sectional direction.

The method of detecting the blood vessel is not particularly limited as long as the blood vessel in the panoramic image can be detected. The blood vessel detection unit 65 can use various methods for detecting the short-axis view of the blood vessel from the panoramic image, such as a method of using a blood vessel determination model by machine learning, and a method of using template matching, as the image analysis processing for detecting the blood vessel shown in the panoramic image. In addition, the blood vessel can also be detected by measuring a blood flow using the Doppler method.

Note that the blood vessel detection unit 65 may detect the blood vessel in the panoramic image, more specifically, the blood vessel in the hidden region in a case where the hidden region detection unit 63 detects that a hidden region is present. Accordingly, only in a case where it is detected that a hidden region is present, a blood vessel in the hidden region is detected. Therefore, there is no need to wastefully perform blood vessel detection processing in a case where it is not detected that a hidden region is present, and thus, it is possible to reduce the processing time and the cost.

In addition, the blood vessel detection unit 65 may detect the blood vessel in the panoramic image for each panoramic image, may detect the blood vessel in the panoramic image once for every plurality of panoramic images, or may obtain an average value of the blood vessels detected from a plurality of panoramic images.

Furthermore, in a case of a blood vessel detection mode described later, the blood vessel detection unit 65 detects the blood vessel in the ultrasound image. In this case, the blood vessel detection unit 65 is operated in the same manner as in a case of detecting the blood vessel in the panoramic image, except for detecting the blood vessel in the ultrasound image instead of the panoramic image.

In a case where the hidden region detection unit 63 detects that the hidden region is present and the blood vessel detection unit 65 detects that the blood vessel is present in the hidden region, the notification unit 67 notifies of various messages regarding the blood vessel.

Although not particularly limited, for example, the notification unit 67 may display various messages on the monitor 41, or may output the messages from a speaker (not illustrated) as an audio, under the control of the display control unit 43. In addition, the notification unit 67 may notify that there is a message by vibrating the apparatus main body 3 using the transducer (not illustrated). Furthermore, the notification unit 67 may perform two or more methods described above in combination.

The condition setting unit 69 sets conditions for the blood vessel as the puncture target.

Conditions are not particularly limited, but may be at least one of upper and lower limit threshold values (for example, xx [mm] or more, yy [mm] or less, and the like) of the diameter of the blood vessel as the puncture target, upper and lower limit threshold values of the depth of the blood vessel as the puncture target, upper and lower limit threshold values of the distance between the blood vessel as the puncture target and the organ (artery, heart, and the like that cannot be punctured) around the blood vessel as the puncture target, or the presence or absence of the disease (blood clot, edema, and the like) of the blood vessel as the puncture target and the blood vessel around the blood vessel as the puncture target.

The diameter of the blood vessel as the puncture target, the depth of the blood vessel as the puncture target, the distance between the blood vessel as the puncture target and the organ around thereof, the presence or absence of the disease of the blood vessel around the blood vessel as the puncture target, and the like can be detected by the image analysis, for example.

The condition setting unit 69 may change the conditions according to an instruction from the user. In other words, the user can change the conditions set in the condition setting unit 69.

The mode switching unit 37 switches the operation mode of the ultrasound diagnostic apparatus between a normal mode, the blood vessel detection mode, and the panoramic blood vessel detection mode, under the control of the apparatus control unit 47.

The normal mode is a mode in which an ultrasound image, which is not a panoramic image, is displayed. In a case of the normal mode, the ultrasound image is displayed by the display control unit 43, but the detection of the blood vessel in the ultrasound image by the blood vessel detection unit 65, and the notification of the message by the notification unit 67 are not performed.

The blood vessel detection mode is a mode in which a blood vessel in an ultrasound image, which is not a panoramic image, is detected. Furthermore, in a case of the blood vessel detection mode, the ultrasound image is displayed by the display control unit 43, the blood vessel in the ultrasound image is detected by the blood vessel detection unit 65, and further, the region of the blood vessel is displayed in an emphasis manner as necessary, but the notification of the message by the notification unit 67 is not performed.

The panoramic blood vessel detection mode is a mode in which the blood vessel in the panoramic image is detected. In a case of the panoramic blood vessel detection mode, the panoramic image is displayed by the display control unit 43, the blood vessel in the panoramic image is detected by the blood vessel detection unit 65, and the message is displayed (notified) by the notification unit 67 as necessary.

The display control unit 43 displays various kinds of information on the monitor 41 under the control of the apparatus control unit 47.

For example, the display control unit 43 displays the ultrasound image or the panoramic image on the display screen of the monitor 41 on the basis of the orientation of the monitor 41. In a case where the monitor 41 is in the laterally long posture, for example, the ultrasound image is displayed in a vertically long posture on the display screen of the monitor 41 in the laterally long posture. On the other hand, in a case where the monitor 41 is in the vertically long posture, the ultrasound image is displayed in the vertically long posture on the display screen of the monitor 41 in the vertically long posture. In this manner, even in a case where the monitor 41 is in the laterally long posture or in the vertically long posture, the ultrasound image is displayed always in the vertically long posture on the display screen of the monitor 41.

In addition, in a case where the posture of the monitor 41 is changed from the laterally long posture to the vertically long posture, or in a case where the posture of the monitor 41 is changed from the vertically long posture to the laterally long posture, the ultrasound image is rotated by 90 degrees around the axis perpendicular to the display screen so as to be displayed always in the vertically long posture on the display screen of the monitor 41. The same applies to the panoramic images.

The input device 45 receives various instructions input from the user. The input device 45 is not particularly limited, but includes, for example, various buttons, and a touch panel or the like which is provided on the display screen of the monitor 41 and through which various instructions are input by the user's touch operation.

The apparatus control unit 47 controls the ultrasound probe 1 and each unit of the apparatus main body 3 on the basis of a program stored in advance and an instruction or the like of the user input from the input device 45.

In the present embodiment, the ultrasound image generation unit 31, the notification processing unit 35, the mode switching unit 37, the display control unit 43, and the apparatus control unit 47 constitute a processor 49.

Next, the operation of the ultrasound diagnostic apparatus in a case of generating the ultrasound image will be described with reference to the flowchart of FIG. 5.

First, in a case where the ultrasound image is generated, in a state where the ultrasound probe 1 is in contact with the examination location of the subject, the transmission of the ultrasonic waves is started and the sound ray signal is generated by the transmission and reception circuit 13, under the control of the apparatus control unit 47 (Step S1).

That is, the ultrasound beams are transmitted to the examination location of the subject from a plurality of transducers of the transducer array 11 according to the drive signals from the pulser 51.

Ultrasound echoes from the examination location based on the ultrasound beams transmitted from the pulser 51 are received by each transducer of the transducer array 11, and the reception signal as an analog signal is output from each transducer of the transducer array 11, which has received the ultrasound echo.

The reception signal output from each transducer of the transducer array 11 is amplified by the amplification unit 53, and is subjected to AD conversion by the AD conversion unit 55, and thereby the reception data is acquired.

Then, by performing the reception focusing processing on the reception data by the beam former 57, the sound ray signal is generated.

Subsequently, under the control of the apparatus control unit 47, the ultrasound image of the examination location of the subject is generated by the ultrasound image generation unit 31 on the basis of the sound ray signal generated by the beam former 57 of the transmission and reception circuit 13 (Step S2).

That is, the sound ray signal generated by the beam former 57 is subjected to various kinds of signal processing by the signal processing unit 21, and the image information data representing tomographic image information regarding tissues inside the subject is generated.

Then, the image information data generated by the signal processing unit 21 is raster-converted by the DSC 23, and is further subjected to various kinds of image processing by the image processing unit 25, and thus the ultrasound image is generated.

Subsequently, under the control of the apparatus control unit 47, predetermined processing is performed on the ultrasound image generated by the image processing unit 25, by the display control unit 43, and the processed ultrasound image is displayed on the monitor 41 (Step S3).

Figure 6:
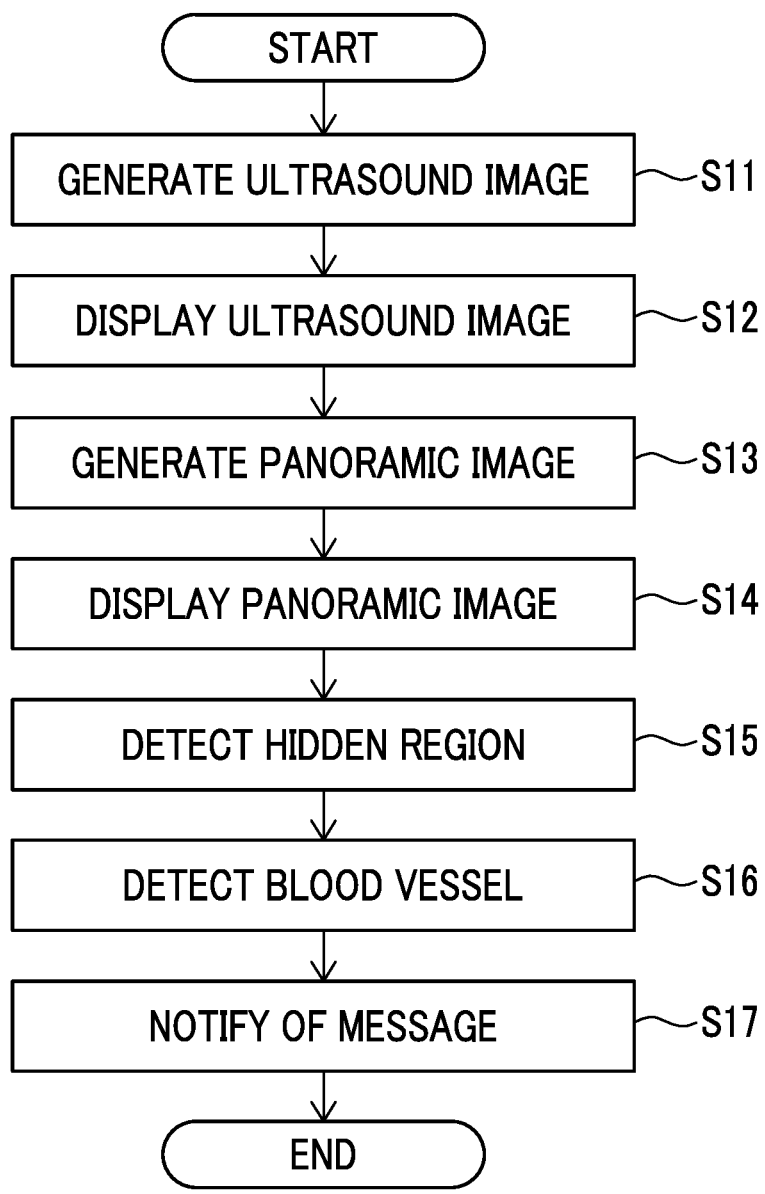
FIG. 6 is a flowchart of an embodiment illustrating an operation of an ultrasound diagnostic apparatus in a case where a user searches for a blood vessel in an ultrasound image in a case of performing blood vessel puncture.

Next, the operation of the ultrasound diagnostic apparatus in a case where the user searches for the blood vessel in the panoramic image in a case of performing the blood vessel puncture will be described with reference to the flowchart illustrated in FIG. 6.

The user can switch the operation mode between the normal mode, the blood vessel detection mode, and the panoramic blood vessel detection mode.

Figure 7:
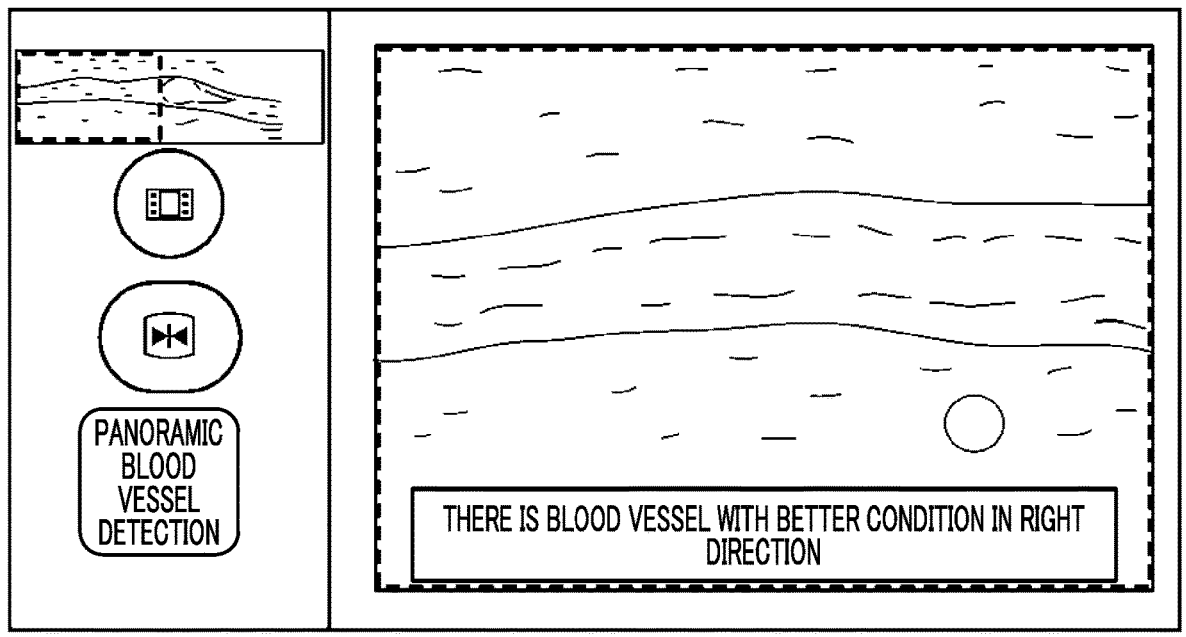
FIG. 7 is a conceptual diagram of an embodiment illustrating a display screen in a case of a panoramic blood vessel detection mode.

FIG. 7 is a conceptual diagram of the embodiment illustrating the display screen in a case of the panoramic blood vessel detection mode. The entire laterally long panoramic image is displayed in a reduced manner at the top left of the display screen illustrated in FIG. 7, and a mode switching button is displayed at the bottom left of the display screen. A partial region of the panoramic image is enlarged and displayed from the central portion to the right portion of the display screen, and a message of "there is blood vessel with a better condition in a right direction" is displayed (notified) at the lower portion of the partial region.

In a case of the panoramic blood vessel detection mode, as illustrated in FIG. 7, a partial region of the enlarged and displayed panoramic image is displayed by being surrounded by a dashed line frame, and a region corresponding to this partial region is displayed by being surrounded by a dashed line frame in the entire panoramic image. Accordingly, the user can easily understand which region of the entire panoramic image is being displayed by checking the position of the dashed line frame displayed in the entire panoramic image.

Figure 8:
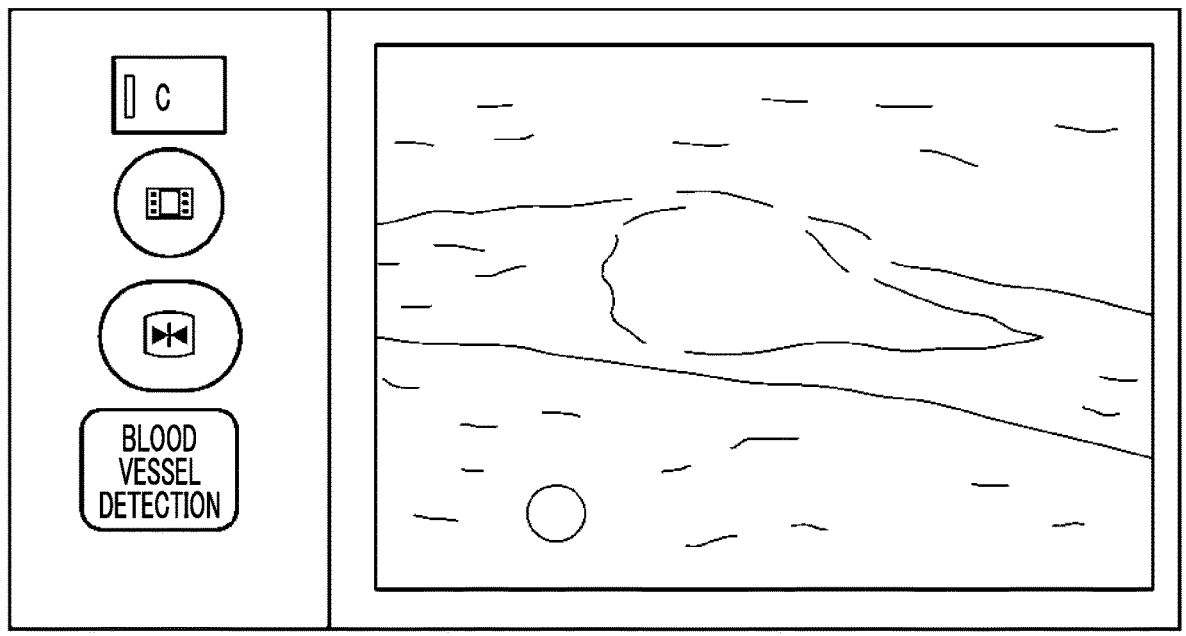
FIG. 8 is a conceptual diagram of an embodiment illustrating a display screen in a case of a blood vessel detection mode.

FIG. 8 is a conceptual diagram of the embodiment illustrating the display screen in a case of the blood vessel detection mode. The mode switching button is displayed at the bottom left of the display screen illustrated in FIG. 8. The ultrasound image is enlarged and displayed from the central portion to the right portion of the display screen.

A current operation mode is displayed on the mode switching button. In a case of the normal mode, "normal" is displayed on the mode switching button. In a case of the panoramic blood vessel detection mode, "panoramic blood vessel detection" is displayed on the mode switching button as illustrated in FIG. 7, and in a case of the blood vessel detection mode, "blood vessel detection" is displayed on the mode switching button as illustrated in FIG. 8. Therefore, the user can easily understand the operation mode by checking the display of the mode switching button.

Figure 9:
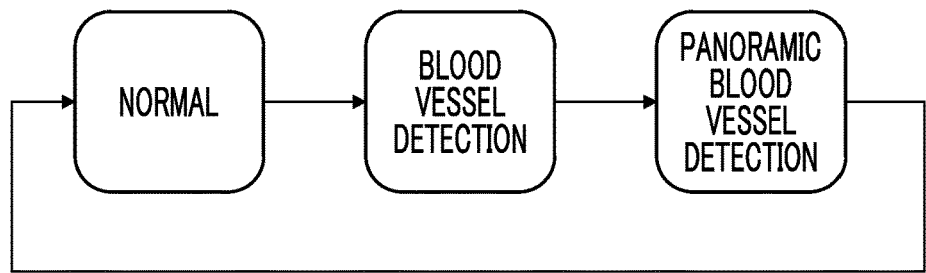
FIG. 9 is a block diagram of an embodiment illustrating a switching order of operation modes.

Each time the user presses the mode switching button by, for example, a touch operation, the mode switching unit 37 switches the operation mode between the normal mode, the blood vessel detection mode, and the panoramic blood vessel detection mode. For example, as illustrated in FIG. 9, the operation mode is sequentially switched from the normal mode to the blood vessel detection mode, from the blood vessel detection mode to the panoramic blood vessel detection mode, and from the panoramic blood vessel detection mode to the normal mode each time the user presses the mode switching button.

For example, in a case of performing the blood vessel puncture while observing the panoramic image, the user selects the panoramic blood vessel detection mode by the touch operation. Accordingly, the operation mode is switched to the panoramic blood vessel detection mode by the mode switching unit 37.

Subsequently, for example, the user searches for the blood vessel (vein) as the puncture target while moving the ultrasound probe 1 in a state where the ultrasound probe 1 is in contact with the body surface of the examination location of the subject, in the width direction of the transducer array 11 of the ultrasound probe 1 along the body surface, by setting the monitor 41 in the vertically long posture or the laterally long posture.

Alternatively, the user searches for the blood vessel as the puncture target while moving the ultrasound probe 1 in a state where the ultrasound probe 1 is in contact with the body surface of the examination location of the subject, in a direction from the body surface toward the inside of the body of the examination location, or in a direction from the inside of the body toward the body surface, by setting the monitor 41 in the vertically long posture or the laterally long posture.

Accordingly, as described above, the ultrasound images including the short-axis view of the blood vessel in the examination location of the subject are sequentially generated by the ultrasound image generation unit 31 (Step S11).

Subsequently, the ultrasound images are sequentially displayed on the display screen of the monitor 41 by the display control unit 43 on the basis of the orientation of the monitor 41 (Step S12).

Note that, in a case of the panoramic blood vessel detection mode, in Step S11, in a case where ultrasound images of a plurality of frames are generated, a panoramic image can be generated by synthesizing the plurality of frames of ultrasound images. Therefore, in Step S12, displaying the ultrasound image on the display screen of the monitor 41 is not necessary, and may be performed as necessary.

On the other hand, various kinds of processing for notifying of the message regarding the blood vessel are performed by the notification processing unit 35.

That is, by the panoramic image generation unit 61, the panoramic image is generated from the ultrasound images of the plurality of frames included in the same tomographic plane formed by moving the ultrasound probe 1 (Step S13).

Subsequently, the panoramic image is displayed on the display screen of the monitor 41 by the display control unit 43 (Step S14).

On the other hand, by the hidden region detection unit 63, whether or not the hidden region that is not displayed on the display screen is present in the panoramic image is detected (Step S15).

In addition, the blood vessel in the panoramic image is detected by the blood vessel detection unit 65 (Step S16). In this case, the blood vessel in the display region detected by the blood vessel detection unit 65 may be displayed in an emphasis manner by the display control unit 43.

Then, in a case where it is detected that a hidden region is present and it is detected that a blood vessel is present in the hidden region, the notification unit 67 notifies of a message regarding the blood vessel (Step S17).

In this manner, in the ultrasound diagnostic apparatus, in a case where it is detected that a hidden region that is not displayed on the display screen is present in the panoramic image and it is detected that a blood vessel is present in the hidden region, a message regarding the blood vessel is notified. Accordingly, since the user can easily understand the state of the blood vessel in the hidden region by displaying the blood vessel in the hidden region according to the content of the message, it is possible to safely and reliably perform the blood vessel puncture.

Next, a case where the hidden region is generated in the panoramic image will be described.

Figure 10:
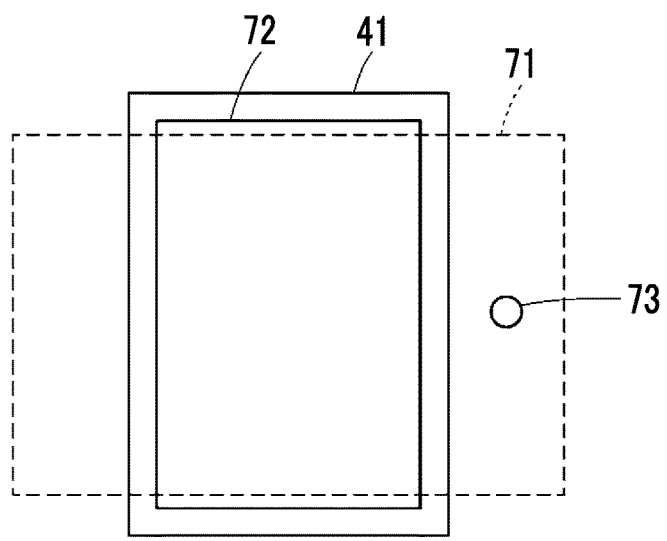
FIG. 10 is a conceptual diagram of an embodiment of a case where a hidden region is generated in a panoramic image.
Figure 11:
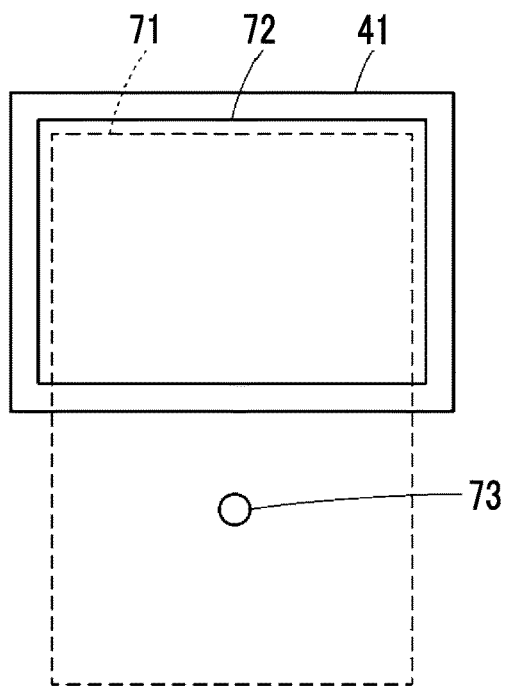
FIG. 11 is a conceptual diagram of an embodiment of a case where a hidden region is generated in a panoramic image.
Figure 12A:
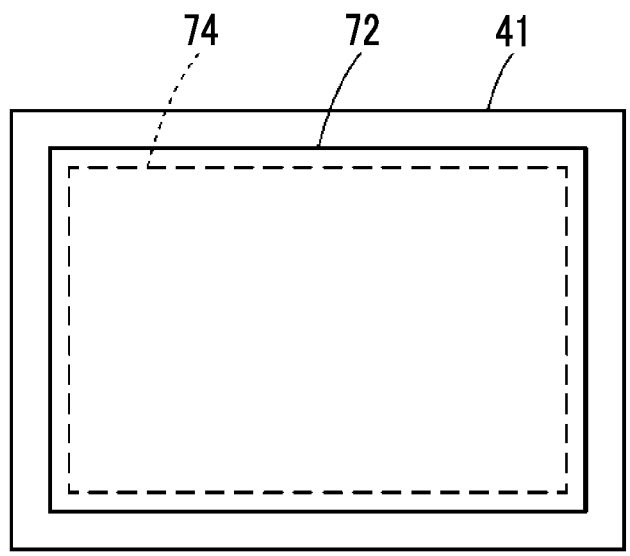
FIG. 12A is a conceptual diagram illustrating a state where a laterally long ultrasound image is displayed to fit within a display screen of a monitor in a laterally long posture.
Figure 12B:
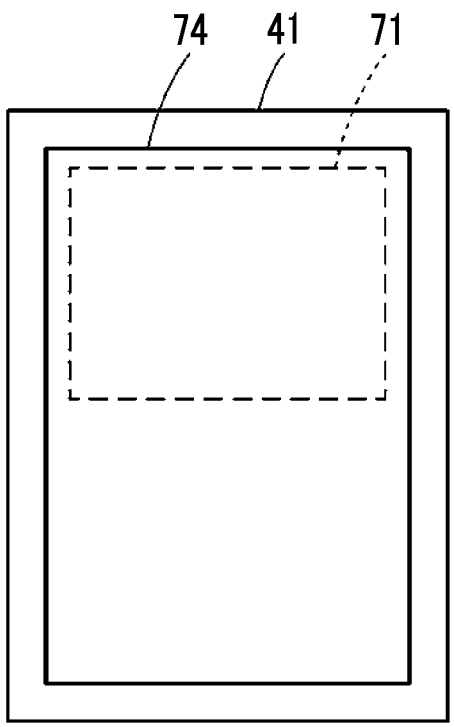
FIG. 12B is a conceptual diagram illustrating a state where a laterally long ultrasound image is displayed in a reduced manner such that the ultrasound image fits within a display screen of a monitor in a vertically long posture.

FIGS. 10 and 11 are conceptual diagrams of the embodiment of a case where a hidden region is generated in the panoramic image. In FIGS. 10 and 11, a panoramic image 71 is indicated by a dashed line, and a display screen 72 is indicated by a solid line.

In the example illustrated in FIG. 10, the monitor 41 is in the vertically long posture, and the panoramic image 71 is displayed by being enlarged until the size in the depth direction matches the size of the display screen 72 in the up and down direction without changing the aspect ratio of the laterally long panoramic image 71. In this example, a hidden region may be generated in a part on both sides of the panoramic image 71 in the width direction depending on the difference between the aspect ratio of the display screen 72 and the aspect ratio of the panoramic image 71.

In the example illustrated in FIG. 11, the monitor 41 is in the laterally long posture, and the panoramic image 71 is displayed by being enlarged until the size in the width direction matches the size of the display screen 72 in the left and right direction without changing the aspect ratio of the vertically long panoramic image 71. Also in this example, a hidden region may be generated on a part on the lower side of the panoramic image 71 in the depth direction depending on the difference between the aspect ratio of the display screen 72 and the aspect ratio of the panoramic image 71.

In this manner, without being limited to the examples in FIGS. 10 and 11, there are various cases in which a hidden region is generated in the panoramic image depending on the difference between the aspect ratio of the display screen and the aspect ratio of the panoramic image.

Next, the method of generating the panoramic image will be described.

The panoramic image generation unit 61 can perform the image analysis on ultrasound image data or ultrasound images of a plurality of frames, and generate a panoramic image from the ultrasound image data or ultrasound images of the plurality of frames on the basis of the result of the image analysis.

For example, in a case where the frame rate is high such as 30 frames/second, it is considered that, even in a case where the user moves the ultrasound probe 1 at a high speed in a case of observing the panoramic image, the ultrasound images of adjacent frames include a common portion (the same portion).

Accordingly, the panoramic image generation unit 61 can detect the common portion in the ultrasound images of the adjacent frames on the basis of the result of the image analysis, and generate a panoramic image by sequentially synthesizing the ultrasound images of a plurality of frames by aligning and superimposing the common portions.

In this case, the hidden region detection unit 63 can detect whether a hidden region is present in the panoramic image by aligning the panoramic image and the ultrasound image (live image) of the current frame, on the basis of the result of the image analysis.

Alternatively, the panoramic image generation unit 61 can perform the image analysis on the ultrasound image data or ultrasound images of a plurality of frames, and generate a panoramic image from the ultrasound image data or ultrasound images of the plurality of frames on the basis of the result of the image analysis and the motion of the ultrasound probe 1 detected by the motion sensor 17.

That is, the panoramic image generation unit 61 can detect the common portion in the ultrasound images of the adjacent frames on the basis of the result of the image analysis and the motion of the ultrasound probe 1, and generate a panoramic image by sequentially synthesizing the ultrasound image data or ultrasound images of a plurality of frames by aligning and superimposing the common portions.

In this case, the hidden region detection unit 63 can detect whether a hidden region is present in the panoramic image by aligning the panoramic image and the ultrasound image of the current frame, on the basis of the result of the image analysis and the motion of the ultrasound probe 1.

By synthesizing the ultrasound images of the plurality of frames by adding the motion of the ultrasound probe 1 to the result of the image analysis, it is possible to synthesize the ultrasound images of the plurality of frames more accurately than synthesizing the ultrasound images of the plurality of frames on the basis of only the result of the image analysis.

Next, ultrasound images used for generating a panoramic image will be described.

For example, in a case where the frame of the current ultrasound image is a frame N, and a panoramic image is generated from the ultrasound images from a frame 1 to the frame N, examples of frames of ultrasound images used for generating a panoramic image include various case including N frames from the frames 1 to N, N−1 frames from the frames 1 to N−1, odd frames of the frames 1, 3, 5, ..., and N−1.

In this manner, the panoramic image generation unit 61 can generate a panoramic image from the ultrasound image data or ultrasound images of a plurality of frames generated within a certain period from the present to the past.

The certain period is not particularly limited, but, for example, the panoramic image generation unit 61 can generate a panoramic image from the ultrasound image data or ultrasound images of the plurality of frames generated within one examination period for performing the examination on the examination location.

One examination period is a period from the start of the end of one examination. The one examination period includes a case where the ultrasound probe 1 is separated from the epidermis and then is brought into contact with the epidermis of the examination location of the subject again, that is, a case where a period in which the ultrasound probe 1 is not in contact with the epidermis of the examination location is included. For example, from the perspective of the continuity of the ultrasound images, it is considered that there is no problem in that the ultrasound image obtained after the ultrasound probe is separated from the epidermis for several seconds and then is brought into contact with the epidermis again is used for generating the panoramic image, but it is considered that it is better not to use the ultrasound image obtained after the ultrasound probe is separated for several minutes or several hours and then is brought into contact with the epidermis again, for generating the panoramic image.

In other words, it is desirable that the panoramic image generation unit 61 generates a panoramic image from the ultrasound image data or ultrasound images of the plurality of frames generated within one contact period in which the ultrasound probe 1 is in contact with the body surface of the examination location.

Next, updating of the panoramic image will be described.

The number of frames of the ultrasound images used in a case of updating the panoramic image may be fixed, or may not be fixed.

The panoramic image generation unit 61 may continuously update the panoramic image for each frame of the ultrasound image. For example, the panoramic image generation unit 61 generates a panoramic image using the ultrasound images of frames 1, 2, and 3 among the ultrasound images generated in the order of frames 1, 2, 3, 4, and ..., and then sequentially updates the panoramic image using the ultrasound images of frames 2, 3, and 4, and frames 3, 4, and 5, for example.

In addition, the panoramic image generation unit 61 may update the panoramic image every certain number of frames of the ultrasound images. For example, in a case of updating a panoramic image every 60 frames of the ultrasound images, the panoramic image generation unit 61 generates a panoramic image using the ultrasound images of frames 1, 2, and 3 among the ultrasound images generated in the order of frames 1, 2, 3, 4, and . . . , and then sequentially updates the panoramic image using the ultrasound images of frames 61, 62, and 63, and frames 121, 122, and 123, for example.

Furthermore, in a case where the ultrasound image data or ultrasound image of the current frame is the ultrasound image data or ultrasound image of the same tomographic plane as the panoramic image, in other words, in a case where a common portion is included in the ultrasound image data or ultrasound image of the current frame and the panoramic image, the panoramic image generation unit 61 may update the panoramic image in a patchwork manner using the ultrasound image data or ultrasound image of the current frame, for example, by aligning and superimposing the common portions.

In this case, for each frame of the ultrasound image, in a case where the ultrasound image data or ultrasound image of the current frame is not the ultrasound image data or ultrasound image of the same tomographic plane, the panoramic image generation unit 61 does not use the ultrasound image data or ultrasound image of the current frame, and in a case where the ultrasound image data or ultrasound image of the current frame is the ultrasound image data or ultrasound image of the same tomographic plane, the panoramic image generation unit 61 sequentially updates the panoramic image in a patchwork manner by sequentially synthesizing the ultrasound image data or ultrasound image of the current frame to the panoramic image.

Note that, the size of the updated panoramic image is not fixed, and is a size corresponding to a maximum movement range in which the ultrasound probe 1 is moved by the user in a case of creating a panoramic image. For example, in a case where the user moves the ultrasound probe 1 in the left and right direction along the body surface in a state where the ultrasound probe 1 is in contact with the body surface of the examination location of the subject, the size of the updated panoramic image is a size corresponding to a range from the left end to the right end of the movement.

Next, the notification of the message by the notification unit 67 will be described.

In a case where it is detected that a blood vessel is present in the hidden region, the notification unit 67 may notify of a message indicating a direction of the blood vessel in the hidden region.

In the example illustrated in FIG. 10, the hidden region is present in a part on both sides of the panoramic image 71 in the width direction, and a blood vessel 73 is present in the hidden region on the right side. In this case, the notification unit 67 notifies of a message such as "there is a blood vessel on the right outer side of the display screen".

Accordingly, the user can be notified that the blood vessel 73 is present on the right outer side of the display screen 72, and accordingly, the blood vessel 73 can be displayed and checked.

In addition, the notification unit 67 may notify of a message for the instruction of a specific operation for displaying the blood vessel in the hidden region within the display region of the panoramic image, which is displayed on the display screen.

To describe with specific examples, in a case where it is detected that a blood vessel is present in the hidden region, the notification unit 67 may notify of a message for the instruction of displaying the panoramic image in a reduced manner.

In the example illustrated in FIG. 11, the hidden region is present in a part on the lower side of the panoramic image 71 in the depth direction, and the blood vessel 73 is present in the hidden region on the lower side. In this case, the notification unit 67 notifies of a message such as "there is still a blood vessel in the depth direction, the blood vessel can be seen in a case of reducing the image".

In addition, the notification unit 67 may notify of a message for the instruction of changing the depth setting of the ultrasound image in a case where it is detected that a hidden region is present in a part on the lower side of the panoramic image in the depth direction.

In the example illustrated in FIG. 11, the notification unit 67 notifies of a message such as "change depth settings to visualize blood vessels at deeper position".

In a case where it is detected that the monitor 41 is in the vertically long posture and it is detected that a hidden region is present in a part of the panoramic image in the width direction, or in a case where it is detected that the monitor 41 is in the laterally long posture and it is detected that a hidden region is present in a part of the panoramic image in the depth direction, the notification unit 67 may notify of a message for the instruction of changing the orientation of the monitor between the vertically long posture and the laterally long posture.

In the example illustrated in FIG. 11, in a case where the panoramic image is displayed in a reduced manner, or in a case where the depth setting of the ultrasound image is changed, the entire panoramic image may be displayed small depending on the orientation of the monitor 41, the aspect ratio of the panoramic image, and the like.

In the example illustrated in FIG. 11, in a case where a virtual rectangular region from the top of the panoramic image to the blood vessel 73 in the hidden region is laterally long, by displaying the laterally long virtual rectangular region in the display region of the monitor 41 in the laterally long posture in a reduced manner, the laterally long virtual rectangular region can be displayed larger than by displaying the laterally long virtual rectangular region in the display region of the monitor 41 in the vertically long posture. Therefore, in this case, it is better not to change the laterally long posture of the monitor 41.

On the other hand, in the example illustrated in FIG. 11, in a case where a virtual rectangular region from the top of the panoramic image to the blood vessel 73 in the hidden region is vertically long, by displaying the vertically long virtual rectangular region in the display region of the monitor 41 in the vertically long posture in a reduced manner, the vertically long virtual rectangular region can be displayed larger than by displaying the vertically long virtual rectangular region in the display region of the monitor 41 in the laterally long posture in a reduced manner. Therefore, in this case, it is better to change the monitor 41 to the vertically long posture.

In this manner, in a case where, by changing the orientation of the monitor 41, the virtual rectangular region can be displayed larger than by displaying the panoramic image in a reduced manner or changing the depth setting of the panoramic image, the notification unit 67 gives priority to changing the orientation of the monitor 41 over displaying the panoramic image in a reduced manner and changing the depth setting, and notifies of a message such as "please rotate the monitor before the display in a reduced manner or the change of the depth setting".

The notification unit 67 may notify of a message for the instruction of moving the ultrasound probe 1 in a direction of the blood vessel in the hidden region.

For example, as illustrated in FIG. 10, in a case where the blood vessel 73 is present in the hidden region on the right side, the notification unit 67 notifies of a message such as "please move the probe to the right side in order to display the blood vessel on the right side". In addition, as illustrated in FIG. 11, in a case where the blood vessel 73 is present in the hidden region on the lower side, the notification unit 67 notifies of a message such as "please move the probe to the lower side in order to display the blood vessel on the lower side".

The notification unit 67 may notify of a message on the basis of the detection result of the blood vessel in the panoramic image, that is, the blood vessel in the display region and the hidden region.

For example, in a case where it is detected that a blood vessel is preset in the display region and it is detected that a blood vessel is present in the hidden region, the notification unit 67 may not notify of a message. In this case, the display control unit 43 may display the blood vessel in the display region in an emphasis manner.

In addition, in a case where it is detected that a blood vessel is present in the display region and the hidden region, the notification unit 67 compares the blood vessel in the display region and the hidden region with the condition for the blood vessel as the puncture target set in the condition setting unit 69, and notifies of a message on the basis of the comparison result. For example, the notification unit 67 notifies of a message regarding whether the blood vessel in the hidden region is better or worse than the blood vessel in the display region, as the condition for the blood vessel as the puncture target.

For example, in a case where the blood vessel in the hidden region on the right side has a better condition than the blood vessel in the display region, the notification unit 67 notifies of a message such as "there is blood vessel with a better condition in a right direction" as illustrated in FIG. 7. In addition, in a case where the blood vessel in the hidden region has a worse condition than the blood vessel in the display region, the notification unit 67 notifies of a message such as "the blood vessel in the display region has a better condition" or "the condition is bad, but there is a blood vessel outside the display screen, so please check".

In addition, in a case where it is not detected that a blood vessel is present in the display region and it is detected that a blood vessel is present in the hidden region, the notification unit 67 notifies of a message regarding the blood vessel as in a case where it is detected that a hidden region is present and it is detected that a blood vessel is present in the hidden region.

Furthermore, in a case where it is not detected that a blood vessel is present in the display region and the hidden region, the notification unit 67 notifies of a message indicating that a blood vessel is not detected, such as "no blood vessel found".

The present invention is not limited to the handheld ultrasound diagnostic apparatus, and may be similarly applicable to a stationary ultrasound diagnostic apparatus, or a portable ultrasound diagnostic apparatus in which the diagnostic apparatus main body 3 is realized by a laptop terminal device. In a case of a stationary or portable ultrasound diagnostic apparatus, a monitor of which the orientation can be changed to the vertically long posture or the laterally long posture by the user rotating the monitor by 90 degrees is provided, and the posture sensor 33 is built in the monitor, and detects whether the orientation (posture) of the monitor is a laterally long posture or a vertically long posture.

In addition, as illustrated in FIG. 1, the apparatus main body 3 may include the ultrasound image generation unit 31, but the present invention is not limited thereto, and the entire ultrasound image generation unit 31 or only the signal processing unit 21 may be provided on the ultrasound probe 1 side.

In the apparatus of the embodiment of the present invention, the hardware configurations of the processing units executing various kinds of processing such as the transmission and reception circuit 13, the ultrasound image generation unit 31, the notification processing unit 35, the display control unit 43, and the apparatus control unit 47 may be dedicated hardware, or may be various processors or computers that execute programs.

The various processors include a central processing unit (CPU) as a general-purpose processor executing software (program) and functioning as various processing units, a programmable logic device (PLD) as a processor of which the circuit configuration can be changed after manufacturing such as a field programmable gate array (FPGA), and a dedicated electric circuit as a processor having a circuit configuration designed exclusively for executing specific processing such as an application specific integrated circuit (ASIC).

One processing unit may be configured by one of the various processors or may be configured by a combination of the same or different kinds of two or more processors, for example, a combination of a plurality of FPGAs or a combination of an FPGA and a CPU). Further, a plurality of processing units may be configured by one of various processors, or two or more of a plurality of processing units may be collectively configured by using one processor.

For example, there is a form where one processor is configured by a combination of one or more CPUs and software as typified by a computer, such as a server and a client, and this processor functions as a plurality of processing units. Further, there is a form where a processor realizing the functions of the entire system including a plurality of processing units by one integrated circuit (IC) chip as typified by a system on chip (SoC) or the like is used.

Furthermore, the hardware configurations of these various processors are more specifically electric circuitry where circuit elements, such as semiconductor elements, are combined.

The method of the embodiment of the present invention can be carried out, for example, by a program for causing a computer to execute each step of the method. Further, a computer-readable recording medium in which this program is recorded can also be provided.

The present invention has been described in detail, but the present invention is not limited to the above-described embodiments, and various improvements and changes may be made within a range not departing from the scope of the present invention.

EXPLANATION OF REFERENCES

1: ultrasound probe
3: apparatus main body
11: transducer array
13: transmission and reception circuit
15: battery
17: motion sensor
21: signal processing unit
23: DSC
25: image processing unit
31: ultrasound image generation unit
33: posture sensor
35: notification processing unit
37: mode switching unit 41: monitor
43: display control unit
45: input device
47: apparatus control unit
49: processor
51: pulser
53: amplification unit
55: AD conversion unit
57: beam former
61: panoramic image generation unit
63: hidden region detection unit
65: blood vessel detection unit
67: notification unit
69: condition setting unit
71: panoramic image
72: display screen
73: blood vessel
74: ultrasound image

What is claimed is:

1. An ultrasound diagnostic apparatus comprising:
an ultrasound probe;
a monitor that has a display screen; and
one or more processors configured to:
generate an ultrasound image from ultrasound image data obtained by performing transmission and reception of an ultrasound beam with respect to an examination location of a subject using the ultrasound probe;
generate a panoramic image from the ultrasound image data or ultrasound images of a plurality of frames included in the same tomographic plane formed by moving the ultrasound probe;
display the panoramic image on the display screen;
detect whether or not a hidden region that is not displayed on the display screen is present in the panoramic image;
a blood vessel in the panoramic image; and
notify of a message in a case where it is detected that the hidden region is present and it is detected that the blood vessel is present in the hidden region.

2. The ultrasound diagnostic apparatus according to claim 1,
wherein the one or more processors are configured to generate the panoramic image from the ultrasound image data or ultrasound images of the plurality of frames generated by moving the ultrasound probe in a width direction of a transducer array of the ultrasound probe along a body surface of the examination location in a state where the ultrasound probe is in contact with the body surface.

3. The ultrasound diagnostic apparatus according to claim 2,
wherein the one or more processors are configured to:
perform image analysis on the ultrasound image data or ultrasound images of the plurality of frames,
generate the panoramic image from the ultrasound image data or ultrasound images of the plurality of frames on the basis of a result of the image analysis, and
detect whether or not the hidden region is present by aligning the panoramic image and the ultrasound image of a current frame on the basis of the result of the image analysis.

4. The ultrasound diagnostic apparatus according to claim 1,
wherein the one or more processors are configured to generate the panoramic image from the ultrasound image data or ultrasound images of the plurality of frames generated by moving the ultrasound probe in a direction from a body surface toward an inside of a body of the examination location or in a direction from the inside of the body toward the body surface in a state where the ultrasound probe is in contact with the body surface of the examination location.

5. The ultrasound diagnostic apparatus according to claim 1,
wherein the one or more processors are configured to:
perform image analysis on the ultrasound image data or ultrasound images of the plurality of frames,
generate the panoramic image from the ultrasound image data or ultrasound images of the plurality of frames on the basis of a result of the image analysis, and
detect whether or not the hidden region is present by aligning the panoramic image and the ultrasound image of a current frame on the basis of the result of the image analysis.

6. The ultrasound diagnostic apparatus according to claim 1,
wherein the ultrasound probe includes a motion sensor that detects a motion of the ultrasound probe, and
the one or more processors are configured to:
perform image analysis on the ultrasound image data or ultrasound images of the plurality of frames,
generate the panoramic image from the ultrasound image data or ultrasound images of the plurality of frames on the basis of a result of the image analysis and the motion of the ultrasound probe, and
detect whether or not the hidden region is present by aligning the panoramic image and the ultrasound image of a current frame on the basis of the result of the image analysis and the motion of the ultrasound probe.

7. The ultrasound diagnostic apparatus according to claim 1,
wherein the one or more processors are configured to generate the panoramic image from the ultrasound image data or ultrasound images of the plurality of frames generated within a certain period from the present to the past.

8. The ultrasound diagnostic apparatus according to claim 7,
wherein the one or more processors are configured to generate the panoramic image from the ultrasound image data or ultrasound images of the plurality of frames generated within one examination period for performing an examination on the examination location.

9. The ultrasound diagnostic apparatus according to claim 8,
wherein the one or more processors are configured to generate the panoramic image from the ultrasound image data or ultrasound images of the plurality of frames generated within one contact period in which the ultrasound probe is in contact with a body surface of the examination location.

10. The ultrasound diagnostic apparatus according to claim 1,
wherein, in a case where the ultrasound image data or ultrasound image of a current frame is ultrasound image data or an ultrasound image of the same tomographic plane as the panoramic image, the one or more processors are configured to update the panoramic image using the ultrasound image data or ultrasound image of the current frame.

11. The ultrasound diagnostic apparatus according to claim 1,
wherein, in a case where it is detected that the blood vessel is present in the hidden region, the one or more processors are configured to notify of a message indicating a direction of the blood vessel in the hidden region.

12. The ultrasound diagnostic apparatus according to claim 1,
wherein, in a case where it is detected that the blood vessel is present in the hidden region, the one or more processors are configured to notify of a message for an instruction of displaying the panoramic image in a reduced manner.

13. The ultrasound diagnostic apparatus according to claim 1,
wherein, in a case where it is detected that the hidden region is present in a part on a lower side of the panoramic image in a depth direction, the one or more processors are configured to notify of a message for an instruction of changing depth setting of the ultrasound image.

14. The ultrasound diagnostic apparatus according to claim 1,
wherein an orientation of the monitor is changeable to a vertically long posture or a laterally long posture,
the ultrasound diagnostic apparatus further includes a posture sensor that detects whether the orientation of the monitor is the vertically long posture or the laterally long posture, and
in a case where it is detected that the monitor is in the vertically long posture and it is detected that the hidden region is present in a part of the panoramic image in a width direction, or in a case where it is detected that the monitor is in the laterally long posture and it is detected that the hidden region is present in a part of the panoramic image in a depth direction, the one or more processors are configured to notify of a message for an instruction of changing the orientation of the monitor between the vertically long posture and the laterally long posture.

15. The ultrasound diagnostic apparatus according to claim 1,
wherein the one or more processors are configured to notify of a message for an instruction of moving the ultrasound probe in a direction of the blood vessel in the hidden region.

16. The ultrasound diagnostic apparatus according to claim 1,
wherein, in a case where it is detected that the blood vessel is present in a display region and it is not detected that a blood vessel is present in the hidden region, the one or more processors do not notify of the message.

17. The ultrasound diagnostic apparatus according to claim 1,
wherein the one or more processors are configured to:
set a condition for a blood vessel as a puncture target, and
in a case where it is detected that the blood vessel is present in a display region and the hidden region, notify of the message on the basis of a comparison result between the blood vessel in the display region and the hidden region and the condition.

18. The ultrasound diagnostic apparatus according to claim 1,
wherein, in a case where it is not detected that a blood vessel is present in a display region and it is detected that the blood vessel is present in the hidden region, the one or more processors are configured to notify of the message.

19. The ultrasound diagnostic apparatus according to claim 1,
wherein, in a case where it is not detected that a blood vessel is present in a display region and the hidden region, the one or more processors are configured to notify of a message indicating that no blood vessel is detected.

20. A control method of an ultrasound diagnostic apparatus, the control method comprising:
a step of generating an ultrasound image from ultrasound image data obtained by performing transmission and reception of an ultrasound beam with respect to an examination location of a subject using an ultrasound probe, via one or more processors;
a step of generating a panoramic image from the ultrasound image data or ultrasound images of a plurality of frames included in the same tomographic plane formed by moving the ultrasound probe, via the one or more processors;
a step of displaying the panoramic image on a display screen of a monitor, via the one or more processors;
a step of detecting whether or not a hidden region that is not displayed on the display screen is present in the panoramic image, via the one or more processors;
a step of detecting a blood vessel in the panoramic image, via the one or more processors; and
a step of notifying of a message, via the one or more processors, in a case where it is detected that the hidden region is present and it is detected that the blood vessel is present in the hidden region.

* * * * *